(12) United States Patent
Schrøder et al.

(10) Patent No.: US 7,195,703 B2
(45) Date of Patent: Mar. 27, 2007

(54) ELECTRODE FOR ANALYTICAL VOLTAMMETRY

(76) Inventors: Knut H. Schrøder, Vilhelm Krags vei 2, N-7023 Trondheim (NO); Öyvind Mikkelsen, Myrsnipeveien 20, N-7082 Kattem (NO)

( * ) Notice: Subject to any disclaimer, the term of this patent is extended or adjusted under 35 U.S.C. 154(b) by 214 days.

(21) Appl. No.: 10/380,517

(22) PCT Filed: Sep. 14, 2001

(86) PCT No.: PCT/NO01/00376

§ 371 (c)(1),
(2), (4) Date: Sep. 30, 2003

(87) PCT Pub. No.: WO02/23179

PCT Pub. Date: Mar. 21, 2002

(65) Prior Publication Data

US 2004/0045820 A1    Mar. 11, 2004

(30) Foreign Application Priority Data

Sep. 15, 2000    (NO) ................................. 20004641

(51) Int. Cl.
G01N 27/333    (2006.01)
(52) U.S. Cl. .................... 205/775; 205/789.5; 205/789
(58) Field of Classification Search ........ 204/416–418, 204/290.08, 290.09, 290.14, 293; 205/775, 205/416

See application file for complete search history.

(56) References Cited

U.S. PATENT DOCUMENTS

| 4,211,623 A | 7/1980 | Ross, Jr. et al. ............ 204/419 |
| 4,936,979 A * | 6/1990 | Brown ........................ 210/85 |
| 5,672,257 A | 9/1997 | Birch et al. ................... 205/43 |
| 5,755,954 A * | 5/1998 | Ludwig et al. ............. 205/794 |

FOREIGN PATENT DOCUMENTS

| DE | 148 987 | | 6/1981 |
| NL | 7611704 A | * | 4/1977 |
| RO | 111807 | | 1/1997 |

OTHER PUBLICATIONS

CAPLUS abstract of Loshchinina et al. ("Effect of the composition of galvanic nickel-cobalt alloys on the overvoltage of hydrogen in alkaline solution,"Doklady Akademii Nauk UzSSR (1958), (No. 2), 39-42).*

(Continued)

Primary Examiner—Alex Noguerola
(74) Attorney, Agent, or Firm—Wenderoth, Lind & Ponack, L.L.P.

(57) ABSTRACT

An electrode for use in analytical voltammetry, wherein the electrode has a uniform composition and contains an alloy in a solid state, the alloy containing a pure metal or compound having a low overvoltage for hydrogen and a few percent of at least one second metal or compound, wherein the electrode is a non-toxic electrode with a sufficiently high overvoltage for hydrogen allowing detection of a metal or compound to be detected. Also provided is an apparatus containing the electrode for performing analytical voltammetry involving a redox reaction at an electrode surface, and a method for increasing the utility of voltammetric analyses, by conducting the analyses with an electrode system containing the electrode.

10 Claims, 6 Drawing Sheets

Detection of zinc on silver with 4 % bismuth alloy electrode. Concentrations were 267, 534 and 800 µg l$^{-1}$. All scan performed in DPASV mode in NH$_4$Ac (0.05 M). Scan rate of 15 mV / s, pulse height 70 mV and a deposition time of two minutes. Current values corrected for offset.

OTHER PUBLICATIONS

CAPLUS abstract of Ling et al. ("Simultaneous determination of Zinc and copper in human serum—anodic stripping voltammetry," Shanghai Diyi Yixueyuan Xuebao (1983), 10(5), 392-6).*

CAPLUS abstract of Kaplin et al. ("Stripping analysis of thin films of silicon dioxide an dhydrofluoric acid for trace impurities of certain elements," Izvestiya Tomskogo Politekhnicheskogo Instituta (1976), 275, 109-12).*

CAPLUS abstract of Vlasov et al. ("Lead-selective electrodes based on lead and silver sulfides," Zhurnal Analiticheskoi Khimii (1979), 34(8), 1522-6).*

CAPLUS abstract of Stoefen ("Dental amalgam. Poison in our mouth," Toxicology (1974), 2(4), 355-8).*

CAPLUS abstract of Kukizaki ("Studies on the effects of dental amalgam on the fertilization and early development of sea urchin eggs (Hemicentrotus pulcherrimus)," Shika Rikogaku Zasshi (1975), 16(35), 123-7).*

CAPLUS abstract of Mayer (The toxicity of mercury and/or amalgam, Deutsche Zahnaerztliche Zeitschrift (1980), 35(4), 450-6).*

Lorscheider et al. ("Mercury exposure from "silver" tooth fillings: emerging evidence questions a traditional dental paradigm," FASEB vol. 9, Apr. 1995, pp. 504-508).*

English language translation of Loshchinina et al. ("Effect of the composition of galvanic nickel-cobalt alloys on the overvoltage of hydrogen in alkaline solution," Doklady Akademii Nauk UzSSR (1958), (No. 2), 39-42).*

Derwent abstract of Moskvin et al. (SU 1580233 A).*

CAPLUS abstract of Matrka et al. ("Analysis of dyes and intermediate products forming during dye manufacture. X. Potentiometric titrations with sodium nitrite using bimetal electrode systems," Collection of Czechoslovak Chemical Communications (1970), 35(3), 995-1000).* pp. 53, 66, and 68, and Figure 6.12 of Sawyer et al. (Electrochemistry for Chemists 2nd ed., John Wiley & Sons, Inc. 1995.*

* cited by examiner

Fig. 1 Cross-section of the metal alloy electrode.

Fig. 2 Sweep from -1200 mV to -200 mV with silver electrode contaminated with 4% bismuth. Insert as a small picture up in the left corner a typical plot of a pure silver electrode. Scan performed in DPASV mode in $NH_4Ac$ (0.05 M). Scan rate of 15 mV / s, and pulse height 70 mV.

Fig. 3 Detection of zinc on silver with 4 % bismuth alloy electrode. Concentrations were 267, 534 and 800 µg l$^{-1}$. All scan performed in DPASV mode in NH$_4$Ac (0.05 M). Scan rate of 15 mV / s, pulse height 70 mV and a deposition time of two minutes. Current values corrected for offset.

Fig. 4 Detection of zinc on silver with 4 % lead(II) oxide alloy electrode. Concentration of zinc was 534 µg l$^{-1}$. All scan performed in DPASV mode in NH$_4$Ac (0.05 M). Scan rate of 15 mV / s, pulse height 70 mV and a deposition time of two minutes.

Fig. 5 Detection of zinc on silver with 4 % mercury alloy electrode. Concentration of zinc was 100, 200, 300 and 400 μg l$^{-1}$. All scan performed in DPASV mode in $NH_4Ac$ (0.05 M). Scan rate of 15 mV / s, pulse height 70 mV and a deposition time of two minutes.

Fig. 6 Detection of zinc and cadmium on silver electrode containing 4 % mercury. Concentrations were 400 µg l$^{-1}$ zinc and 200 µg l$^{-1}$ cadmium. The scan was performed in DPASV mode in NH$_4$Ac (0.05 M). Scan rate of 15 mV / s, pulse height 70 mV and a deposition time of two minutes.

ELECTRODE FOR ANALYTICAL VOLTAMMETRY

INTRODUCTION

The present invention relates to an electrode for use in electrochemical analysis and electrochemical processes, especially in analytical voltammetry.

Liquid mercury and liquid diluted mercury amalgams have been the major electrode systems employed in voltammetry and related methods. This is mainly due to their high overvoltage to hydrogen, which enables the determination of heavy metals (zinc, nickel and cobalt etc.) and other species with high negative half wave potentials.

Mercury has been, since the development of polarography, the most used electrode material in voltammetric techniques[1]. The main reason for this is that a new fresh electrode surface is formed for each mercury droplet. Mercury has however, the added advantages that it has a high overvoltage towards hydrogen and that the formation of diluted amalgams prevents the formation of intermetallic compounds in many cases.

Due to the toxicity of mercury, its use is now restricted and may be prohibited, even for analytical purposes. It is necessary therefore, to develop new electrode materials to meet the need for a non-toxic electrode material in voltammetry.

Numerous papers dealing with alternative electrodes and techniques have been published recently. Among these the glassy carbon electrode[2], graphite electrode[3-5], gold electrode[6], silver electrode[7,8], and bismuth electrode[9] are important contributions. But, except from the bismuth electrode, there is a main drawback for these types of electrodes; their use is limited below −800 mV, restricted by the lack of hydrogen overvoltage.

The present authors have recently invented a method to substitute mercury with dental amalgam and related solid compounds[10] in electrode systems. It has been found that such systems have a very high overvoltage to hydrogen, allowing for trace analyses at potentials sufficiently negative to allow determination of e.g. zinc, cobalt, nickel and iron at trace levels. This has not previously been possible except through use of mercury, or mercury film electrodes. Such determinations are very important for field and online analyses of pollutants in soil and ground-water, and the electrode may be used repeatedly.

The phenomena governing hydrogen overvoltage have their foundation in those mechanisms by which the hydrogen evolution reaction occurs for a given metal. Important factors are the steps in the evolution of hydrogen, the energy of the metal-hydrogen bond, the dependence of the surface coverage by hydrogen on the over potential, the double-layer structure, and the pre-exponential factors of the kinetic equation for the slow stage of the process[11]. The way by which the electrode material or the electrode-surface affects these factors is not properly known. Some important trends are however identified:

For metals such as lead, mercury, thallium, cadmium, bismuth etc, which possess high hydrogen overvoltage, an increase in the exchange current density is found with increased hydrogen adsorption energy. This means that the current density at the equilibrium potential increases for these metals, with increased strength of the bond of hydrogen to metal. Accordingly a low coverage with hydrogen is found at their surface and the rate-determining step must be the proton discharge reaction.

For metals such as platinum, rhenium, rhodium, tungsten, iridium, molybdenum, etc. high values of hydrogen-adsorption energy is observed and a decrease in the exchange current density is found with an increase in the hydrogen adsorption energy, and high hydrogen coverage[12].

SUMMARY OF THE INVENTION

The present invention has been conceived to provide a solution to the problems with prior art electrodes as described above.

In accordance with a first aspect of the invention there is provided an electrode for use in electrochemical analysis or electrochemical processes. The electrode comprises an alloy in a solid state, the alloy comprising a pure metal or compound having a low overvoltage for hydrogen and a few percent of at least one second metal or compound, obtaining an electrode with a sufficiently high overvoltage for hydrogen allowing detection of a metal or compound to be detected.

In accordance with a second aspect of the invention there is provided a means for performing electrochemical analyses or electrochemical processes involving a redox reaction at an electrode surface, comprising an analysis cell, a system of electrodes arranged in the analysis cell filled with a solution to be analysed producing a measuring signal as a consequence of a redox reaction at the electrodes, wherein the measuring signal is a measure of the concentration of a component in the solution. At least one of the electrodes comprises an alloy in a solid state, the alloy comprising a pure metal or compound having a low overpotential for hydrogen and a few percent of at least one second metal or compound, obtaining an electrode with a sufficiently high overpotential for hydrogen allowing detection of a metal or compound to be detected.

In accordance with a third aspect of the invention there is provided a method for increasing the utility of voltammetric analyses. The method comprising using an electrode system comprising at least one electrode of alloy in a solid state, the alloy comprising a pure metal or compound having a low overvoltage for hydrogen and a few percent of at least one second metal or compound, obtaining an electrode with a sufficiently high overvoltage for hydrogen allowing detection of a metal or compound to be detected.

The pure metal or compound may be metallic silver, gold, copper or platinum or another metal or compound with too low overvoltage for hydrogen to be used alone for a certain analytical purpose. Mercury, bismuth or lead oxide or another metal or compound with the effect of increasing the resulting overvoltage for hydrogen, may be used as the second metal or compound.

In a preferred embodiment the alloy comprises less than 10% of the second metal or compound. In an even more preferred embodiment of the invention the alloy comprises about 4% of the second metal or compound.

The electrode may be used as a measuring electrode or any other electrodes in an electroanalytical method, requiring high overvoltage for hydrogen, as a measuring electrode in voltammetric analysis, preferably of the type differential pulse anodic stripping voltammetry.

Electrode materials with a metal or a compound with low hydrogen overvoltage change their hydrogen overvoltage properties substantially when contaminated with even small amounts of metals or compounds possessing high hydrogen overvoltage. This extends greatly the range of potentially available electrode systems and thereby analytical possibilities of voltammetry.

The voltammetric behaviour of some non-toxic electrodes that have been contaminated with small amounts of metals or compounds possessing high hydrogen overvoltage was investigated. It was found that these electrodes increase their hydrogen overvoltage dramatically. This means, for instance, that the noble metals may be given a high hydrogen overvoltage. This allows for now opportunities in voltammetry and related methods. Not only as a large number of different undoubtedly non-toxic electrode metals and electrode compounds may be available, but such systems also allow for the development of customise electrodes for specific analyses.

The counter electrode may also be made from a composite compound in order to act as a reservoir for the re-plating of the electrode surface. In this way a new electrode surface may be generated prior to each scan. Such results have also been demonstrated in previous work using pure silver electrodes[13].

The invention is stated in the appended claims.

BRIEF DESCRIPTION OF DRAWINGS

Embodiments of the invention will now be described in the following with reference to the accompanying drawings, where.

DETAILED DESCRIPTION OF THE INVENTION

Experimental

Figure 1:
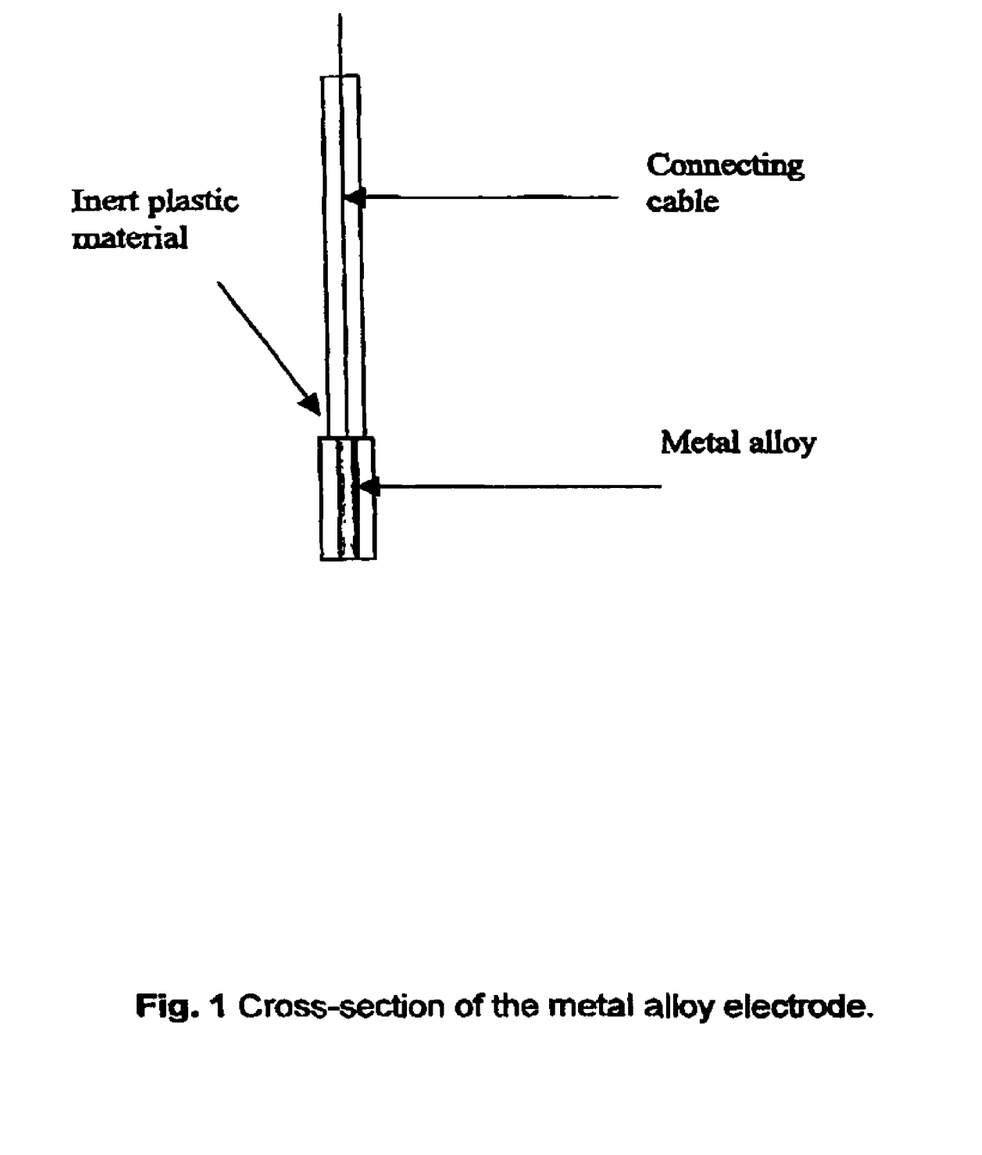
FIG. 1 shows a cross section of a metal alloy electrode according to an embodiment of the invention.

Three distinct silver-based electrodes were produced in connection with this preliminary paper. These were contaminated with four percent bismuth, four percent lead oxide and four percent mercury, respectively (all by weight). The electrodes were prepared by simply mixing powdered samples of the given in a mixing capsule. The capsule was subsequently installed in a mixer and mixed for 30 seconds. The alloy was than transferred to a quartz tube (internal diameter 4 mm) which was then evacuated and sealed. The sealed quartz tube was then transferred to an oven preheated to 1000° C., where the metal alloy was melted and kept for 2 min. The alloy was thereafter allowed to cool down and solidify. The quartz tube was subsequently crushed, and the final metal alloy cylinder retrieved and sealed inside an inert plastic membrane in such a way that only a small surface was exposed. Finally, the electrode end was cleanly cut and polished once using a fine soften sandpaper, and washed in water purified by Millipore Elix and then with Millipore Milli-Q Gradient system (Millipore Corporation, SA 67120 Molsheim France). The electrode is shown in FIG. 1.

All experiments were performed in $NH_4Ac$ (0.05 M, pH 6). A three-electrode system where the potential was measured vs. a silver/silver chloride/saturated silver chloride/saturated potassium chloride reference electrode was used. The counter electrode in these preliminary tests was a platinum wire, however a counter electrode with same alloy composition as the working electrode may also be used.

The custom voltammetric equipment was constructed in our laboratories. This comprises a digital device capable of performing all modes of voltammetry. This equipment has been described previously[14]. All reagents were of analytical grade.

The working alloy electrodes were polished prior to the experiments and then used without any maintenance during the experiment over a period of ca one week.

All of the analyses reported in this preliminary paper were performed as differential pulse anodic stripping voltammetry (DPASV), with a scan rate of 15 mV/S, pulse height 70 mV and a deposition time of two minutes.

3. Results

This section is divided into three parts. The first part shows results obtained using an electrode with an alloy composed of silver (96%) and bismuth (4%). The second part summarises results from a mixture of silver (96%) and lead(II) oxide (4%), and the third part gives the result from an alloy containing silver (96%) and mercury (4%).

3-1 Silver electrode with 4% Bismuth

Figure 2:
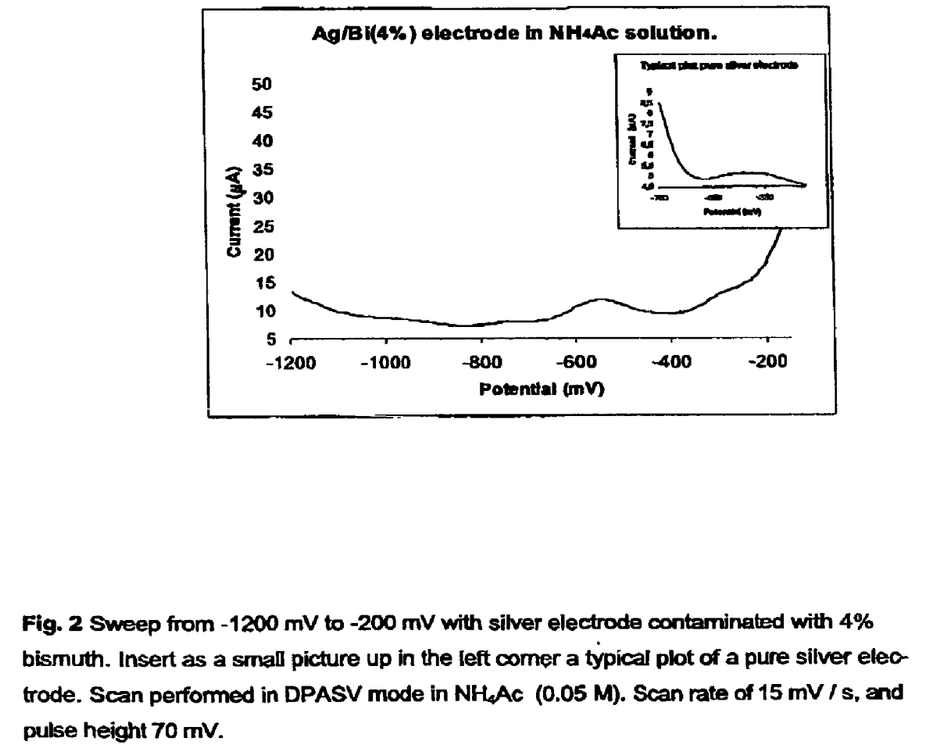
FIG. 2 is a plot of a sweep from −1200 mV to −200 mV with a silver electrode contaminated with 4% bismuth according to an embodiment of the invention.

The voltammetric scan was performed as described in section 2. Both deposition and start potential was −1200 mV. FIG. 2 shows a typical plot of a blank $NH_4Ac$ (0.05 M) solution. In FIG. 2 a sweep is performed from −1200 mV to −200 mV with a silver electrode contaminated with 4% bismuth. Insert as a small picture up in the left corner a typical plot of a pure silver electrode. The scan was performed in DPASV mode in $NH_4Ac$ (0.05 M), with a scan rate of 15 mV/s, and pulse height 70 mV.

Figure 3:
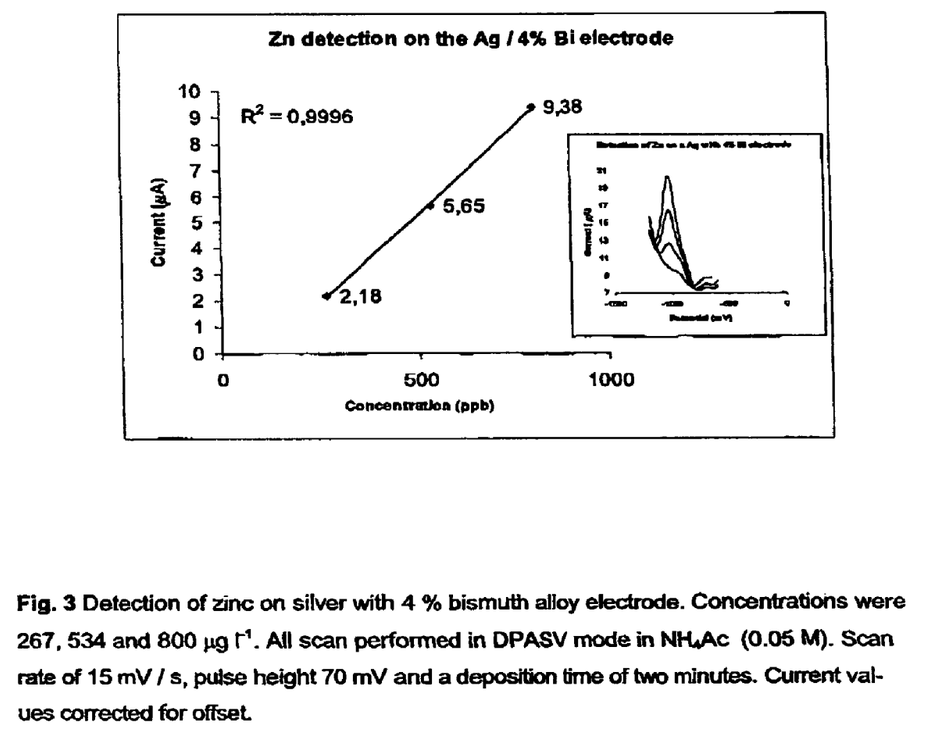
FIG. 3 is a plot showing detection of zinc on the electrode in FIG. 2.

A pure silver electrode may normally be used down to about −750 mV, before the current increases dramatically due to the hydrogen formation, as shown in the small frame up in the left corner in FIG. 2. There is no doubt that the addition of small amount of bismuth gives the silver alloy electrode a high over potential. Some analyses were performed to detect zinc on this type of electrode. Three different concentrations were detected by the standard addition method. Zinc standard solution (50 mg l$^{-1}$, 400 μl) was added to $NH_4Ac$ (0.05 M, 75 ml) solution in three sequential steps giving zinc concentrations of 267, 534 and 800 μg l$^{-1}$. A voltammetric scan was run after each addition. The peak heights for zinc were measured and corrected for offset, and presented in FIG. 3. In FIG. 3 detection of zinc on silver with 4% bismuth alloy electrode is shown. Concentrations were 267, 534 and 800 μg l$^{-1}$. All scans were performed in DPASV mode in $NH_4Ac$ (0.05 M), with a scan rate of 15 mV/s, pulse height 70 mV and a deposition time of two minutes. Current values were corrected for offset. As a small frame up in the right corner in FIG. 3, is shown detection of zinc on the silver electrode with 4% bismuth, but as current (μA) as a function of potential (mV).

3.2 Silver Electrode with 4% PbO

Figure 4:
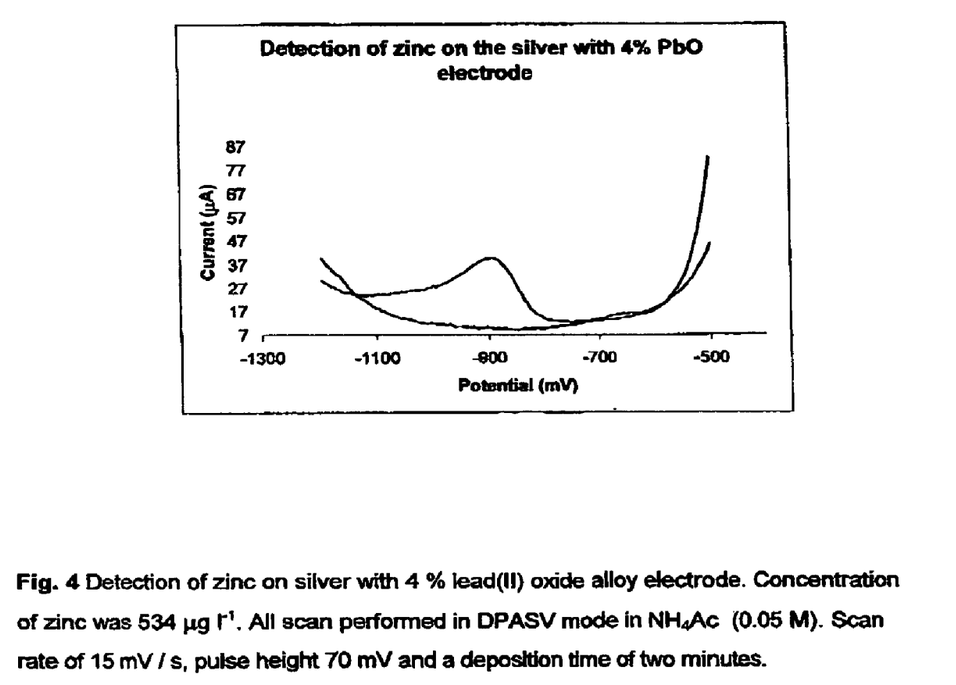
FIG. 4 is a plot showing detection of zinc on a silver electrode contaminated with 4% lead(II) oxide according to an embodiment of the invention.

The voltammetric scan was performed as described in section 2. Both deposition and start potential was −1200 mV. FIG. 4 shows a typical plot of a blank $NH_4Ac$ (0.05 M) solution and corresponding when zinc was added. As shown there is a high hydrogen over-voltage also on this electrode, as for the silver electrode containing 4% bismuth described in section 3.1. In FIG. 4, detection of zinc on silver with 4% lead(II) oxide alloy electrode is shown as a plot of current (μA) as a function of potential (mV). The concentration of zinc was 534 μg l$^{-1}$. All scans were performed in DPASV mode in NH$_4$Ac (0.05 M), with a scan rate of 15 mV/s, pulse height 70 mV and a deposition time of two minutes.

When the zinc concentration exceeded 500 ppb, a change in the voltammogram was detected around –1100 mV. This change may represent the formation of intermetallic compound. This phenomenon was not observed on the silver electrode with bismuth in section 3.1.

Detection of cadmium was also impossible on this electrode because of the huge current level raising from ca. –600 mV, due to the grate amount of lead inside the electrode.

3.3 Silver Electrode with 4% Mercury

Figure 5:
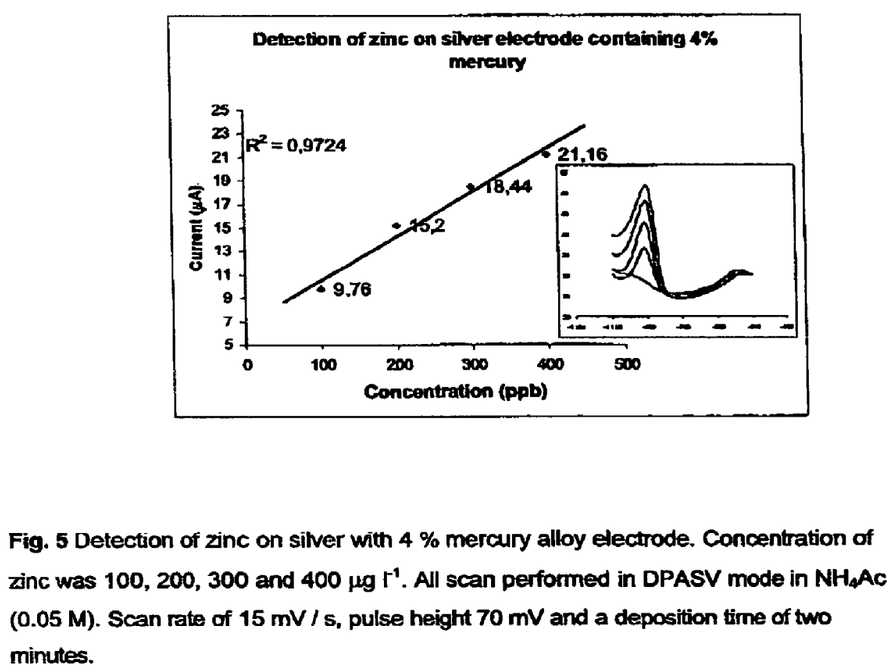
FIG. 5 is a plot showing detection of zinc using a silver electrode contaminated with 4% mercury according to an embodiment of the invention.

Analyses as in section 3.1 and 3.2 were performed for a silver electrode containing ca. four percent mercury. FIG. 5 below shows the result from zinc detection on this type of electrode. Four different concentrations were detected by the standard addition method. Zinc standard solution (50 mg l$^{-1}$, 150 μl) was added to NH$_4$Ac (0.05 M, 75 ml) solution in three sequential steps giving zinc concentrations of 100, 200, 300 and 400 μg l$^{-1}$. A voltammetric scan was run after each addition. In FIG. 5 detection of zinc on silver with 4% mercury alloy electrode is shown as a plot of current (μA) as a function of concentration (ppb). The concentration of zinc was 100, 200, 300 and 400 μg l$^{-1}$. All scans were performed in DPASV mode in NH$_4$Ac (0.05 M), with a scan rate of 15 mV/s, pulse height 70 mV and a deposition time of two minutes. As a small frame to the right is shown a plot of current (μA) vs. potential (mV) for the main plot in FIG. 5.

A high degree of linearity was registered. This is indicated by the relative high $R^2$ ($R^2$=0,9724) coefficient between the experimental data end the applied linear fit in each case.

Figure 6:
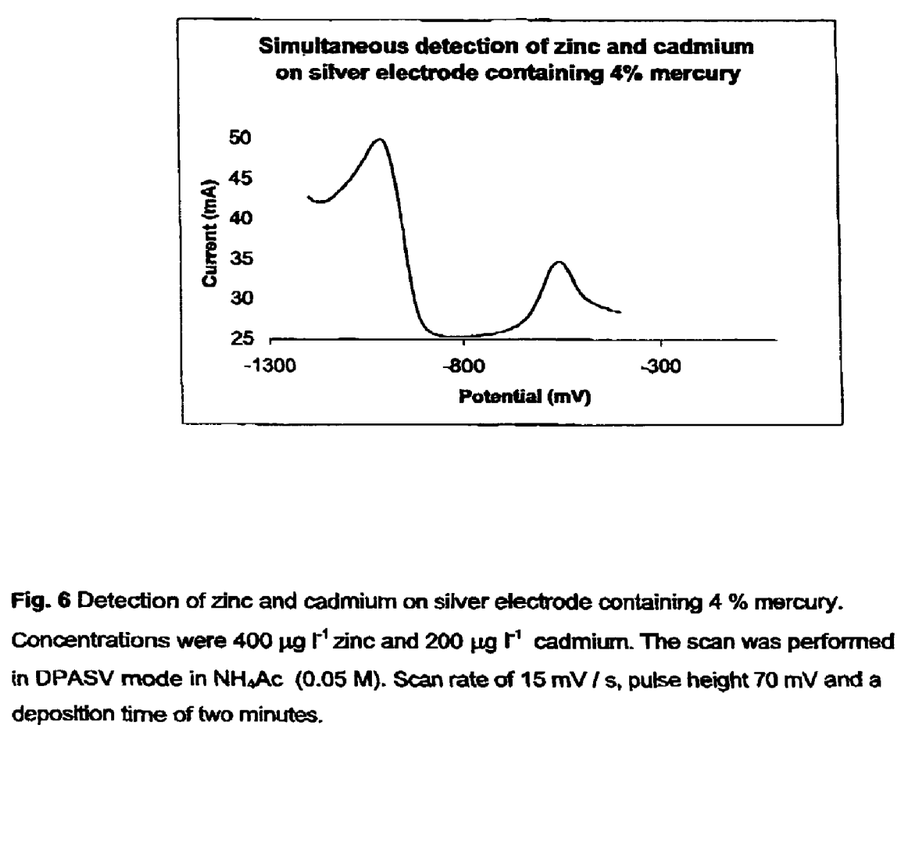
FIG. 6 is a plot showing simultaneous detection of zinc and cadmium on the electrode in FIG. 5.

Also a detection of cadmium (200 ppb) was performed in a NH$_4$Ac (0.05 M) solution containing zinc (400 ppb), and are shown in FIG. 6. In FIG. 6 detection of zinc and cadmium on silver electrode containing 4% mercury is shown as a plot of the resulting current (μA) as a function of potential (mV). Concentrations were 400 μg l$^{-1}$ zinc and 200 μg l$^{-1}$ cadmium. The scan was performed in DPASV mode in NH$_4$Ac (0.05 M), with a scan rate of 15 mV/s, pulse height 70 mV and a deposition time of two minutes. The addition of cadmium had only an insignificant influence on the peak height for zinc.

4. Conclusions

Results in this present paper shows that electrode materials comprising a metal or a compound with low hydrogen overvoltage change their hydrogen overvoltage properties substantially when contaminated with even small amounts of metals or compounds which show high hydrogen overvoltage. This extends greatly the range of potentially available non-toxic electrode systems and thereby analytical possibilities of voltammetry and related methods, also for online use in the field.

A very important point is that the counter electrode in a three-electrode system may be prepared with the same composition as the working electrode. Then a new film may be plated prior to each new scan with material from the counter electrode. With that a new working electrode surface may be generated continuously.

The specific composition of an electrode may be prepared in such a way that it is optimal for some metals, particular considering the possibility to prevent intermetallic compounds.

Having described preferred embodiments of the invention it will be apparent to those skilled in the art that other embodiments incorporating the concepts may be used. These and other examples of the invention illustrated above are intended by way of example only and the actual scope of the invention is to be determined from the following claims.

REFERENCES

1 Douglas A. Skoog, Donald M. West, F. A. James Holler, *Fundamentals of Analytical Chemistry*, 7$^{th}$ Ed., Harcourt Brace Jovanovich Ltd. Fort Worth, 1996.
2 E Fischer, CMG vandenBerg, *Analytica Chimica Acta*, 1999, 385, 1–3, 273.
3 CA Borgo, RT Ferrari, LMS Colpini, CMM Costa, ML Baesso, AC Bento, Analytica Chimica Acta, 1999, 385, 1–3, 103.
4 M Korolczuk, *Fresenius Journal of Analytical Chemistry*, 1997, 357, 4, 389.
5 M Fujimoto, Y Kida, T Nohma, M Takahashi, K Nishio, T Saito, *Journal of Power Sources*, 1996, 63, 1, 127.
6 Y Bonfil, M Brand, E KirowaEisner, *Analytica Chimica Acta*, 1999, 387, 1, 85.
7 O Cavalleri, A M Bittner, H. Kind, K. Kern, *Zeitschrift Fur Physikalische Chemie—International Journal of Research in Physical Chemistry & Chemical Physics*, 1999, 208, 1–2, 107.
8 Øyvind Mikkelsen, Knut H. Schrøder, *Electroanalysis*, 2000, In press.
9 J Wang, J M Lu, S B Hocevar, P A M Farias, B Ogorevc, *Analytical Chemistry*, 2000, 72, 14, 3218–3222.
10 Mikkelsen, Øyvind and Schrøder, Knut H., *Analytical Letters*, 2000, 33, 15.
11 D. R. Crow, *Principles and applications of electrochemistry*, Blackie Academic & Professional 4. Ed, 1994.
12 Andrzej Wieckowski, *Interfacial electrochemistry, theory, experiments, and applications*, Marcel Dekker, Inc., Basel, Switzerland, 1999.
13 Mikkelsen, Øyvind and Schrøder, Knut H., *Electroanalysis*, 2000, In press.
14 Mikkelsen, Øyvind and Schrøder, Knut H., *Electroanalysis*, 2000, 12, 15.

The invention claimed is:

1. A method for increasing the utility of voltammetric analyses, which comprises conducting the analyses with an electrode system comprising at least one electrode comprising an alloy in a solid state, the alloy comprising a mixture of gold with less than 10% by weight of bismuth, or a mixture of silver with less than 10% by weight of bismuth, wherein the electrode is a non-toxic electrode with a sufficiently high overvoltage for hydrogen allowing detection of a metal or compound to be detected.

2. The method according to claim 1, wherein the alloy comprises about 4% by weight of bismuth.

3. The method according to claim 1, wherein the voltammetric analysis is of the type differential pulse anodic stripping voltammetry.

4. The method according to claim 1, wherein the alloy comprises a mixture of silver with less than 10% by weight of bismuth.

5. The method according to claim 1, wherein the alloy comprises a mixture of gold with less than 10% by weight of bismuth.

6. A method which comprises performing voltammetric analysis using an electrode system comprising at least one electrode, wherein a working electrode material of the at least one electrode consists of a solid alloy of gold with less than 10% by weight of bismuth, or a solid alloy of silver with less than 10% by weight of bismuth.

7. The method according to claim 6, wherein the amount of bismuth is about 4% by weight.

8. The method according to claim 6, wherein the voltammetric analysis is of the type differential pulse anodic stripping voltammetry.

9. The method according to claim 6, wherein the alloy comprises a mixture of silver with less than 10% by weight of bismuth.

10. The method according to claim 6, wherein the alloy comprises a mixture of gold with less than 10% by weight of bismuth.

* * * * *